United States Patent [19]

Burch

[11] Patent Number: 5,041,483
[45] Date of Patent: Aug. 20, 1991

[54] PREVENTION OF ODOR GENERATION DURING GAMMA-IRRADIATION OF POLYPROPYLENE FIBERS

[75] Inventor: George N. B. Burch, Covington, Ga.

[73] Assignee: Hercules Incorporated, Wilmington, Del.

[21] Appl. No.: 176,963

[22] Filed: Apr. 4, 1988

Related U.S. Application Data

[63] Continuation of Ser. No. 888,271, Jul. 21, 1986, abandoned.

[51] Int. Cl.$^5$ .............................................. C08L 23/00
[52] U.S. Cl. ................................... 524/274; 524/270; 524/583
[58] Field of Search ......................... 524/270, 274, 283

[56] References Cited

U.S. PATENT DOCUMENTS

| | | | |
|---|---|---|---|
| 3,079,312 | 2/1963 | Alsys | 204/154 |
| 3,313,754 | 4/1967 | Logan | 524/274 |
| 3,463,752 | 8/1969 | Bornstein | 524/274 |
| 3,567,487 | 3/1971 | Poppe et al. | 524/274 |
| 3,598,776 | 8/1971 | Schirmer | 524/274 |
| 3,663,488 | 5/1972 | Kail | 524/274 |
| 3,798,118 | 3/1974 | Jones | 524/274 |
| 3,929,702 | 12/1975 | Miller et al. | 524/274 |
| 4,048,376 | 9/1977 | Unmuth | 524/274 |
| 4,067,938 | 1/1978 | Jack | 524/274 |
| 4,071,656 | 1/1978 | Miller et al. | 524/274 |
| 4,110,185 | 8/1978 | Williams et al. | 204/154 |
| 4,274,932 | 6/1981 | Williams et al. | 204/159.2 |
| 4,279,659 | 7/1981 | Unmuth | 524/274 |
| 4,340,513 | 7/1982 | Motcki et al. | 524/274 |
| 4,460,445 | 7/1984 | Rekers | 204/159.2 |
| 4,467,065 | 8/1984 | Williams et al. | 524/296 |

FOREIGN PATENT DOCUMENTS

| | | | |
|---|---|---|---|
| 0078603 | 11/1983 | European Pat. Off. | |
| 1050802 | 12/1966 | United Kingdom | |
| 1061366 | 3/1967 | United Kingdom | 524/274 |
| 2057458 | 4/1981 | United Kingdom | 524/274 |

Primary Examiner—Joseph L. Schofer
Assistant Examiner—J. M. Reddick
Attorney, Agent, or Firm—John E. Crowe

[57] ABSTRACT

Rosin esters are used to reduce the tendency of shaped articles made from polypropylene, especially fibers, to form malodorous decomposition products upon sterilization by gamma-irradiation. Other stabilizers normally used to prevent discoloration and degradation of polyolefins may also be present. Stabilized fibers are used for the manufacture of disposable medical products.

5 Claims, No Drawings

PREVENTION OF ODOR GENERATION DURING GAMMA-IRRADIATION OF POLYPROPYLENE FIBERS

This application is a continuation of application Ser. No. 888,271, filed July 21, 1986 now abandoned.

FIELD OF THE INVENTION

This invention relates to stabilized polypropylene compositions useful in preparing shaped articles having a reduced tendency toward the accumulation of malodorous decomposition products during and following exposure to gamma-radiation from a cobalt 60 source. This invention especially relates to the use of a rosin ester to stabilize disposable, radiation-sterilized fibrous products for medical applications against the generation of odors.

BACKGROUND OF THE INVENTION

Cobalt 60 gamma-irradiation has become an accepted sterilization technique for medical devices. A dose rate of 2.5 Mrads is customary, although dosages as high as 5.5 Mrads may be used. For shaped polymeric articles such as syringes, tubing, tissue culture flasks, packaging film, etc., degradation during or subsequent to irradiation results in problems such as embrittlement, discoloration and reduced heat and light stability.

U.S. Pat. Nos. 4,110,185, 4,274,932 and 4,467,065 disclose stabilization of polymers against embrittlement during or subsequent to irradiation by incorporating a mobilizer such as a hydrocarbon oil, halogenated hydrocarbon oil, phthalic ester oil, vegetable oil, or silicone oil.

European patent application 78,603 discloses the use of a hindered amine or its salt, N-oxide, N-hydroxide or N-nitroxide to stabilize polyolefin medical articles, e.g., syringes, against yellowing and/or embrittlement resulting from radiation sterilization.

British Patent 1,050,802 discloses the use of a stabilizer system comprising an organic carboxylic acid, e.g., adipic or benzoic acid, and an organic phosphite for articles such as disposable syringes made from radiation sterilizable polyolefin compositions.

U.S. Pat. No. 4,460,445 discloses an olefinic polymer composition containing a hindered phenolic stabilizer and a benzaldehyde acetal which is resistant to degradation when subjected to sterilizing amounts of radiation.

It is known to use polypropylene fibers for medical applications such as gauze, bottle stuffing, a component of nonwoven products such as surgical gowns and operating room barriers, and in combination with other fibers in fabrics. These products, packaged in plastic films, paper envelopes or glass vials, have been sterilized by irradiation, a method which is both economical and convenient. However, a major obstacle to commercial acceptance of these fibrous products is the disagreeable odor generated upon irradiation. Odor may also be a problem in polypropylene shaped articles other than fibers, e.g. molded articles, film for packaging, etc. None of the prior art stabilizer systems addresses the problem of odor generation.

SUMMARY OF THE INVENTION

It has now been found that certain types of cyclic unsaturated compounds can be used as odor-suppressing stabilizers for polypropylene compositions. The composition of this invention, useful in preparing a shaped article having a reduced tendency toward odor generation upon sterilization of the article by gamma-irradiation, comprises a major amount of polypropylene and from about 0.095 to about 1.0% by weight of a rosin ester as a stabilizer. Other stabilizers normally used to prevent degradation of polyolefins may also be present.

DETAILED DESCRIPTION OF THE INVENTION

Analysis of irradiated polypropylene fibers suggests that the liberated odor-producing entities may be oxidation fragments having a low molecular weight and high vapor pressure, e.g., formic, acetic or butyric acids, generated by scission of the polymer chain.

The stabilizers of this invention, useful for suppressing the tendency of polypropylene shaped articles to form malodorous decomposition produces during or following radiation sterilization, are rosin esters inclusive of lower alkyl esters such as methyl, ethyl and propyl, and are characterized by the presence of non-conjugated double bonds within their cyclic structures. Although we do not intend to limit the present invention by theoretical considerations, it is believed that these stabilizers may be preferentially attacked by ozone and/or oxygen during irradiation, thereby reducing the amount of malodorous low molecular weight products split off from the polymer chain. The stabilizers of this invention are effective in maintaining good physical properties in the finished product as well as providing odor control.

The rosin from which the odor-suppressing stabilizers of this invention are derived is generally defined on page 586 of Hackh's Chemical Dictionary, 4th edition, and is inclusive of any of the commercially available types of rosin such as wood rosin, gum rosin, tall oil rosin and mixtures thereof in their crude or refined state. The term "rosin" as used here also includes modified rosins such as partially hydrogenated rosin and partially disproportionated rosin.

The rosin esters useful as the odor-suppressing stabilizers of this invention are preferably esters of a monohydric alcohol and rosin acids such as abietic acid. The methyl ester of rosin and the methyl ester of hydrogenated rosin are most preferred.

The odor suppressing stabilizers are present in the composition of this invention in amounts of from about 0.095 to about 1.0% by weight. An amount of from about 0.095 to about 0.50% by weight is preferred.

In addition to the odor-suppressing stabilizer, other stabilizers commonly used to prevent degradation of polyolefins may also be present. These may include an antioxidant, a prodegradant to reduce the molecular weight of the polymer and improve processability, a light stabilizer, and/or an antacid to protect processing equipment. Examples of antioxidants, prodegradants, light stabilizers and antacids suitable for use with polyolefins are well known to those skilled in the art. While such other additives may be helpful, they are not essential for the purposes of this invention.

The polypropylene is preferably used in flake form, i.e. a powder resembling flour, to facilitate dispersion of the odor-suppressing stabilizer, and any other additives that may be used, in the polymer. Additives do not mix well with other commercially available forms of polypropylene, e.g., polypropylene chips. Preferably polypropylene is mixed with such additives in an impact blender and the mixture is then extruded and shaped, e.g., by spinning.

The polypropylene used in the composition of this invention is characterized by a crystallinity of from about 55% to about 65%, a weight average molecular weight $M_w$ of from about $3.0 \times 10^5$ to about $4.0 \times 10^5$, a molecular weight distribution of from about 5.0 to about 8.0 and a melt flow of from about 2.5 to about 4.0 g/10 minutes at 230° C.

All percentages in the following examples are % by weight, based on the total weight of the composition.

EXAMPLE 1

96.23% Polypropylene in flake form (crystallinity 60%, $M_w$ $3.5 \times 10^5$, molecular weight distribution 6.4, melt flow 3.2 g/10 min.) is mixed in an impact blender with 0.06% 1,3,5-tris(4-tert butyl-3-hydroxy-2,6-dimethylbenzyl)-1,3,5-triazene-2,4,6-(1H,3H,5H)-tri as an antioxidant, 0.10% calcium stearate as an antacid, 0.034% 2,5-dimethyl-2,5-di(t-butylperoxy) hexane as a prodegradant, 0.097% poly-[6-[(1,1,3,3-tetramethyl-butyl)-amino]-1,3,5-triazine-2,4-diyl [2-(2,2,6,6-tetramethylpiperidyl)-imino]-hexamethylene-[4-(2,2,6,6-tetramethylpiperidyl)-imino] as a light stabilizer and, as the odor-suppressing stabilizer, 0.096% of a methyl ester of rosin having a Gardner-Holdt viscosity at 25° C. of Y-Z3 and an acid number of 6. The peroxide prodegradant, a liquid, is first absorbed on the polypropylene flake and is added to the blender as a 2% mixture with polypropylene.

After blending, the mixture of polypropylene and additives is fed to a 1½ inch extruder and spun through a 210 hole spinnerette at 285° C. maximum melt temperature to form 690 denier spun yarns which, in turn, were drawn to 385 denier continuous filament yarns at feed and draw roll temperatures of 60° and 115° C.

Samples consisting of 10 g of drawn yarn are placed individually into each of three types of containers commonly used to package fibrous medical products: paper envelopes, one quart polyethylene bags, and 2 oz. screw-top glass jars. The yarns are sealed in their various packages and exposed to gamma-radiation at a rate of 0.21 Mrads per hour for a total of 2.5 Mrads and at a rate of 0.40 Mrads per hour for a total of 5.5 Mrads.

After two weeks of ambient storage following irradiation, the odor of the yarns in their various packages are rated by a 6 member sensory evaluation panel. The results are given in Table 1. Control A is polypropylene flake without any additives. Control B is a composition containing the same amounts of polypropylene flake, antioxidant, antacid, prodegradant and light stabilizer as Example 1, but no odor-suppressing stabilizer. The ratings for the yarn samples in the glass jars give the best indication of the efficacy of the odor-suppressing stabilizer, since the odor cannot dissipate through the jars. Evaluation time is limited to approximately 15 minutes per session. An interval of at least one hour is scheduled between successive evaluations. The values given in the first six columns of Table 1 are averages of the ratings of the six sensory evaluation panelists, based on a scale of 0-10, where 10 is odor-free. Guidelines for the selection and training of sensory panel members are given in ASTM STP 758.

EXAMPLE 2

A composition identical to the one described in Example 1, except for the use of a hydrooenated methyl ester of rosin having a Gardner-Holdt viscosity of Z-Z4 at 25° C. and an acid number of 7 as the odor-suppressing stabilizer, is prepared. The composition is spun, drawn and irradiated as described in Example 1. The odor of the irradiation-sterilized fibers prepared from this composition is rated by a sensory evaluation panel as described in Example 1. The results are given in Table 1.

TABLE 1

|  | 2.5 Mrads Total | | | 5.5 Mrads Total | | | |
| --- | --- | --- | --- | --- | --- | --- | --- |
|  | Paper | Plastic | Glass* | Paper | Plastic | Glass* | Overall Average |
| Example 1 | 5.5 | 4.1 | 4.5 | 5.5 | 4.0 | 4.3 | 4.65 |
| Example 2 | 5.5 | 4.8 | 5.1 | 5.5 | 3.9 | 4.3 | 4.85 |
| Control A | 5.5 | 3.3 | 2.3 | 5.5 | 2.9 | 3.6 | 3.77 |
| Control B | 4.5 | 4.3 | 3.5 | 5.0 | 3.2 | 3.0 | 3.92 |

*A difference of 1.0 is considered significant.

What I claim and desire to protect by Letters Patent is:

1. A method for reducing the tendency of a polypropylene shaped article toward odor generation upon sterilization of the article by gamma-irradiation, comprising incorporating into an article-forming composition from about 0.095 to about 1.0% by weight of a rosin ester as a stabilizer before forming the article.

2. A method for reducing the tendency of articles containing polypropylene to generate malodofous decomposition products upon undergoing radiation sterilization, comprising incorporating into a corresponding article-forming composition about 0.095% to about 0.50% by weight of an ester of a monohydric lower alkyl alcohol and a rosin acid, said ester having a Gardner-Holdt viscosity at 25° C. of Y-Z3 and an acid number of 6.

3. A method for reducing the tendency of articles containing polypropylene to generate malodorous decomposition products upon undergoing radiation sterilization, comprising incorporating into a corresponding article-forming composition about 0.095% to about 0.50% by weight of an ester of a monohydric lower alkyl alcohol and a rosin acid, said ester having a Gardner-Holdt viscosity at 25° C. of Z-Z4 and an acid number of 7.

4. A method according to claim 3 wherein said ester is a methyl ester of a monocarboxy rosin acid.

5. A method according to claim 2 wherein said ester is a methyl ester of a monocarboxy rosin acid.

* * * * *

UNITED STATES PATENT AND TRADEMARK OFFICE
CERTIFICATE OF CORRECTION

PATENT NO.  : 5,041,483
DATED       : August 20, 1991
INVENTOR(S) : George N. B. Burch It is certified that error appears in the above-identified patent and that said Letters Patent is hereby corrected as shown below:

Col. 2, line 17, "produces" should read --products--;

Col. 3, line 16, "...(1H,3H,5H)-tri" should read --...(1H,3H,5H)-trione--; and

Col. 4, line 7, "hydrooenated" should read --hydrogenated--.

Signed and Sealed this

Twentieth Day of July, 1993

Attest:

MICHAEL K. KIRK

Attesting Officer

Acting Commissioner of Patents and Trademarks